United States Patent
Mathis et al.

(10) Patent No.: US 7,503,932 B2
(45) Date of Patent: Mar. 17, 2009

(54) MITRAL VALVE ANNULOPLASTY DEVICE WITH VENA CAVA ANCHOR

(75) Inventors: Mark L. Mathis, Fremont, CA (US); Gregory Nieminen, Bothell, WA (US); Nathan Aronson, Chico, CA (US); Garrett Beget, Bothell, CA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 388 days.

(21) Appl. No.: 11/279,352

(22) Filed: Apr. 11, 2006

(65) Prior Publication Data

US 2007/0239270 A1    Oct. 11, 2007

(51) Int. Cl.
*A61F 2/06* (2006.01)
(52) U.S. Cl. ..................... 623/2.36; 623/2.37
(58) Field of Classification Search ........ 623/2.36–2.37
See application file for complete search history.

(56) References Cited

U.S. PATENT DOCUMENTS

| | | | |
|---|---|---|---|
| 3,974,526 A | 8/1976 | Dardik et al. | |
| 3,995,623 A | 12/1976 | Blake et al. | |
| 4,055,861 A | 11/1977 | Carpentier et al. | |
| 4,164,046 A | 8/1979 | Cooley | |
| 4,485,816 A | 12/1984 | Krumme | |
| 4,550,870 A | 11/1985 | Krumme et al. | |
| 4,588,395 A | 5/1986 | Lemelson | |
| 4,830,023 A | 5/1989 | de Toledo et al. | |
| 5,061,277 A | 10/1991 | Carpentier et al. | |
| 5,099,838 A | 3/1992 | Bardy | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,433,727 A | 7/1995 | Sideris | |
| 5,441,515 A | 8/1995 | Khosravi et al. | |
| 5,449,373 A | 9/1995 | Pinchasik et al. | |
| 5,454,365 A | 10/1995 | Bonutti | |
| 5,458,615 A | 10/1995 | Klemm et al. | |

(Continued)

FOREIGN PATENT DOCUMENTS

EP    0893133    1/1999

(Continued)

OTHER PUBLICATIONS

Mathis et al., U.S. Appl. No. 11/782,490 entitled "Device and method for modifying the shape of a body organ," filed Jul. 24, 2007.

(Continued)

*Primary Examiner*—Suzette J Gherbi
(74) *Attorney, Agent, or Firm*—Shay Glenn LLP

(57) ABSTRACT

The present invention relates to a medical device and uses thereof that supports or changes the shape of tissue near a vessel in which the device is placed. The present invention is particularly useful in reducing mitral valve regurgitation by changing the shape of or supporting a mitral valve annulus. The device includes a support structure, a proximal anchor adapted to be positioned in a superior vena cava, and a distal anchor adapted to be positioned in a coronary sinus. The support structure engages a vessel wall to change the shape of tissue adjacent the vessel in which the intravascular support is placed.

21 Claims, 8 Drawing Sheets

U.S. PATENT DOCUMENTS

| | | | |
|---|---|---|---|
| 5,474,557 A | 12/1995 | Mai | |
| 5,507,295 A | 4/1996 | Skidmore | |
| 5,514,161 A | 5/1996 | Limousin | |
| 5,554,177 A | 9/1996 | Kieval et al. | |
| 5,562,698 A | 10/1996 | Parker | |
| 5,584,867 A | 12/1996 | Limousin et al. | |
| 5,601,600 A | 2/1997 | Ton | |
| 5,676,671 A | 10/1997 | Inoue | |
| 5,733,325 A | 3/1998 | Robinson et al. | |
| 5,741,297 A | 4/1998 | Simon | |
| 5,752,969 A | 5/1998 | Cunci et al. | |
| 5,824,071 A | 10/1998 | Nelson et al. | |
| 5,836,882 A | 11/1998 | Frazin | |
| 5,871,501 A | 2/1999 | Leschinsky et al. | |
| 5,891,193 A | 4/1999 | Robinson et al. | |
| 5,895,391 A | 4/1999 | Farnholtz | |
| 5,899,882 A | 5/1999 | Waksman et al. | |
| 5,908,404 A | 6/1999 | Elliott | |
| 5,928,258 A | 7/1999 | Khan et al. | |
| 5,935,161 A | 8/1999 | Robinson et al. | |
| 5,954,761 A | 9/1999 | Machek et al. | |
| 5,961,545 A | 10/1999 | Lentz et al. | |
| 5,978,705 A | 11/1999 | KenKnight et al. | |
| 5,984,944 A | 11/1999 | Forber | |
| 6,007,519 A | 12/1999 | Rosselli | |
| 6,015,402 A | 1/2000 | Sahota | |
| 6,022,371 A | 2/2000 | Killion | |
| 6,027,517 A | 2/2000 | Crocker et al. | |
| 6,053,900 A | 4/2000 | Brown et al. | |
| 6,077,295 A | 6/2000 | Limon et al. | |
| 6,077,297 A | 6/2000 | Robinson et al. | |
| 6,080,182 A | 6/2000 | Shaw et al. | |
| 6,096,064 A | 8/2000 | Routh | |
| 6,099,549 A | 8/2000 | Bosma et al. | |
| 6,099,552 A | 8/2000 | Adams | |
| 6,129,755 A | 10/2000 | Mathis et al. | |
| 6,171,320 B1 | 1/2001 | Monassevitch | |
| 6,183,512 B1 | 2/2001 | Howanec et al. | |
| 6,190,406 B1 | 2/2001 | Duerig et al. | |
| 6,210,432 B1 | 4/2001 | Solem et al. | |
| 6,228,098 B1 | 5/2001 | Kayan et al. | |
| 6,241,757 B1 | 6/2001 | An et al. | |
| 6,254,628 B1 | 7/2001 | Wallace et al. | |
| 6,267,783 B1 | 7/2001 | Letendre et al. | |
| 6,275,730 B1 | 8/2001 | KenKnight et al. | |
| 6,312,446 B1 | 11/2001 | Huebsch et al. | |
| 6,334,864 B1 | 1/2002 | Amplatz et al. | |
| 6,342,067 B1 | 1/2002 | Mathis et al. | |
| 6,345,198 B1 | 2/2002 | Mouchawar et al. | |
| 6,352,553 B1 | 3/2002 | van der Burg et al. | |
| 6,352,561 B1 | 3/2002 | Leopold et al. | |
| 6,358,195 B1 | 3/2002 | Green et al. | |
| 6,395,017 B1 | 5/2002 | Dwyer et al. | |
| 6,402,781 B1 * | 6/2002 | Langberg et al. | 623/2.36 |
| 6,419,696 B1 | 7/2002 | Ortiz et al. | |
| 6,442,427 B1 | 8/2002 | Boute et al. | |
| 6,503,271 B2 | 1/2003 | Duerig et al. | |
| 6,537,314 B2 | 3/2003 | Langberg et al. | |
| 6,562,067 B2 | 5/2003 | Mathis | |
| 6,569,198 B1 | 5/2003 | Wilson et al. | |
| 6,589,208 B2 | 7/2003 | Ewers et al. | |
| 6,599,314 B2 | 7/2003 | Mathis et al. | |
| 6,602,288 B1 | 8/2003 | Cosgrove et al. | |
| 6,602,289 B1 | 8/2003 | Colvin et al. | |
| 6,623,521 B2 | 9/2003 | Steinke et al. | |
| 6,626,899 B2 | 9/2003 | Houser et al. | |
| 6,629,534 B1 | 10/2003 | St. Goar et al. | |
| 6,629,994 B2 | 10/2003 | Gomez et al. | |
| 6,643,546 B2 | 11/2003 | Mathis et al. | |
| 6,648,881 B2 | 11/2003 | KenKnight et al. | |
| 6,652,538 B2 | 11/2003 | Kayan et al. | |
| 6,656,221 B2 | 12/2003 | Taylor et al. | |
| 6,676,702 B2 | 1/2004 | Mathis | |
| 6,709,425 B2 | 3/2004 | Gambale et al. | |
| 6,716,158 B2 | 4/2004 | Raman et al. | |
| 6,718,985 B2 | 4/2004 | Hlavka et al. | |
| 6,721,598 B1 | 4/2004 | Helland et al. | |
| 6,723,038 B1 | 4/2004 | Schroeder et al. | |
| 6,733,521 B2 | 5/2004 | Chobotov et al. | |
| 6,743,219 B1 | 6/2004 | Dwyer et al. | |
| 6,764,510 B2 | 7/2004 | Vidlund et al. | |
| 6,773,446 B1 | 8/2004 | Dwyer et al. | |
| 6,776,784 B2 | 8/2004 | Ginn | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 6,805,128 B1 * | 10/2004 | Pless et al. | 128/898 |
| 6,810,882 B2 | 11/2004 | Langberg et al. | |
| 6,821,297 B2 | 11/2004 | Snyders | |
| 6,824,562 B2 | 11/2004 | Mathis et al. | |
| 6,827,690 B2 | 12/2004 | Bardy | |
| 6,881,220 B2 | 4/2005 | Edwin et al. | |
| 6,899,734 B2 | 5/2005 | Castro et al. | |
| 6,908,478 B2 | 6/2005 | Alferness et al. | |
| 6,935,404 B2 | 8/2005 | Duerig et al. | |
| 6,949,122 B2 | 9/2005 | Adams et al. | |
| 6,960,229 B2 | 11/2005 | Mathis et al. | |
| 6,964,683 B2 | 11/2005 | Kowalsky et al. | |
| 6,966,926 B2 | 11/2005 | Mathis | |
| 6,976,995 B2 | 12/2005 | Mathis et al. | |
| 7,144,363 B2 * | 12/2006 | Pai et al. | 600/16 |
| 7,152,605 B2 | 12/2006 | Khairkhahan et al. | |
| 2001/0018611 A1 | 8/2001 | Solem et al. | |
| 2001/0041899 A1 | 11/2001 | Foster | |
| 2001/0044568 A1 | 11/2001 | Langberg et al. | |
| 2001/0049558 A1 | 12/2001 | Liddicoat et al. | |
| 2002/0016628 A1 | 2/2002 | Langberg et al. | |
| 2002/0042621 A1 | 4/2002 | Liddicoat et al. | |
| 2002/0042651 A1 | 4/2002 | Liddicoat et al. | |
| 2002/0049468 A1 | 4/2002 | Streeter et al. | |
| 2002/0055774 A1 | 5/2002 | Liddicoat | |
| 2002/0065554 A1 | 5/2002 | Streeter | |
| 2002/0087173 A1 | 7/2002 | Alferness et al. | |
| 2002/0095167 A1 | 7/2002 | Liddicoat et al. | |
| 2002/0138044 A1 | 9/2002 | Streeter et al. | |
| 2002/0151961 A1 | 10/2002 | Lashinski et al. | |
| 2002/0156526 A1 | 10/2002 | Hlavka et al. | |
| 2002/0161377 A1 | 10/2002 | Rabkin et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2002/0188170 A1 | 12/2002 | Santamore et al. | |
| 2003/0018358 A1 | 1/2003 | Saadat | |
| 2003/0069636 A1 | 4/2003 | Solem et al. | |
| 2003/0078465 A1 | 4/2003 | Pai et al. | |
| 2003/0078654 A1 | 4/2003 | Taylor et al. | |
| 2003/0083613 A1 | 5/2003 | Schaer | |
| 2003/0088305 A1 | 5/2003 | Van Schie et al. | |
| 2003/0130730 A1 | 7/2003 | Cohn et al. | |
| 2003/0135267 A1 | 7/2003 | Solem et al. | |
| 2003/0171776 A1 | 9/2003 | Adams et al. | |
| 2003/0236569 A1 | 12/2003 | Mathis et al. | |
| 2004/0010305 A1 | 1/2004 | Alferness et al. | |
| 2004/0019377 A1 | 1/2004 | Taylor et al. | |
| 2004/0039443 A1 | 2/2004 | Solem et al. | |
| 2004/0073302 A1 | 4/2004 | Rourke et al. | |
| 2004/0098116 A1 | 5/2004 | Callas et al. | |
| 2004/0102839 A1 | 5/2004 | Cohn et al. | |
| 2004/0102840 A1 | 5/2004 | Solem et al. | |
| 2004/0111095 A1 | 6/2004 | Gordon et al. | |
| 2004/0127982 A1 | 7/2004 | Machold et al. | |
| 2004/0133220 A1 | 7/2004 | Lashinski et al. | |
| 2004/0133240 A1 | 7/2004 | Adams et al. | |

| | | | | | | |
|---|---|---|---|---|---|---|
| 2004/0133273 | A1 | 7/2004 | Cox | JP | 2003-503101 | 1/2003 |
| 2004/0138744 | A1 | 7/2004 | Lashinski et al. | JP | 2003-521310 | 7/2003 |
| 2004/0148019 | A1 | 7/2004 | Vidlund et al. | WO | WO 98/56435 A1 | 12/1998 |
| 2004/0148020 | A1 | 7/2004 | Vidlund et al. | WO | WO 00/44313 A1 | 8/2000 |
| 2004/0148021 | A1 | 7/2004 | Cartledge et al. | WO | WO 00/60995 A2 | 10/2000 |
| 2004/0153147 | A1 | 8/2004 | Mathis | WO | WO 00/74603 A1 | 12/2000 |
| 2004/0158321 | A1 | 8/2004 | Reuter et al. | WO | WO 01/00111 A1 | 1/2001 |
| 2004/0176840 | A1 | 9/2004 | Langberg | WO | WO 01/50985 A1 | 7/2001 |
| 2004/0193191 | A1 | 9/2004 | Starksen et al. | WO | WO 01/54618 A1 | 8/2001 |
| 2004/0193260 | A1 | 9/2004 | Alferness et al. | WO | WO 01/87180 A2 | 11/2001 |
| 2004/0220654 | A1 | 11/2004 | Mathis et al. | WO | WO 02/00099 A2 | 1/2002 |
| 2004/0220657 | A1 | 11/2004 | Nieminen et al. | WO | WO 02/01999 A2 | 1/2002 |
| 2004/0243227 | A1 | 12/2004 | Starksen et al. | WO | WO 02/05888 A1 | 1/2002 |
| 2004/0249452 | A1 | 12/2004 | Adams et al. | WO | WO 02/19951 A1 | 3/2002 |
| 2004/0260342 | A1 | 12/2004 | Vargas et al. | WO | WO 02/34118 A2 | 5/2002 |
| 2005/0004667 | A1 | 1/2005 | Swinford et al. | WO | WO 02/47539 A2 | 6/2002 |
| 2005/0010240 | A1 | 1/2005 | Mathis et al. | WO | WO 02/053206 A2 | 7/2002 |
| 2005/0021121 | A1 | 1/2005 | Reuter et al. | WO | WO 02/060352 A1 | 8/2002 |
| 2005/0027351 | A1 | 2/2005 | Reuter et al. | WO | WO 02/062263 A2 | 8/2002 |
| 2005/0027353 | A1 | 2/2005 | Alferness et al. | WO | WO 02/062270 A1 | 8/2002 |
| 2005/0033419 | A1 | 2/2005 | Alferness et al. | WO | WO 02/062408 A2 | 8/2002 |
| 2005/0038507 | A1 | 2/2005 | Alferness et al. | WO | WO 02/076284 A2 | 10/2002 |
| 2005/0060030 | A1* | 3/2005 | Lashinski et al. .......... 623/2.37 | WO | WO 02/078576 A2 | 10/2002 |
| 2005/0065598 | A1 | 3/2005 | Mathis et al. | WO | WO 02/096275 A2 | 12/2002 |
| 2005/0085903 | A1* | 4/2005 | Lau ........................... 623/2.11 | WO | WO 03/015611 A2 | 2/2003 |
| 2005/0096666 | A1 | 5/2005 | Gordon et al. | WO | WO 03/049647 A1 | 6/2003 |
| 2005/0096740 | A1 | 5/2005 | Langberg et al. | WO | WO 03049648 A2 | 6/2003 |
| 2005/0107810 | A1 | 5/2005 | Morales et al. | WO | WO 03/059198 A2 | 7/2003 |
| 2005/0119673 | A1 | 6/2005 | Gordon et al. | WO | WO 03/063735 A2 | 8/2003 |
| 2005/0137449 | A1 | 6/2005 | Nieminen et al. | WO | WO 2004/045463 A2 | 6/2004 |
| 2005/0137450 | A1 | 6/2005 | Aronson et al. | WO | WO 2004/084746 | 10/2004 |
| 2005/0137451 | A1 | 6/2005 | Gordon et al. | WO | WO 2005/046531 | 5/2005 |
| 2005/0137685 | A1 | 6/2005 | Nieminen et al. | WO | WO 2006/002492 A1 | 1/2006 |
| 2005/0149179 | A1 | 7/2005 | Mathis et al. | | | |
| 2005/0149180 | A1 | 7/2005 | Mathis et al. | | | |
| 2005/0149182 | A1 | 7/2005 | Alferness et al. | | | |
| 2005/0177228 | A1 | 8/2005 | Solem et al. | | | |
| 2005/0187619 | A1 | 8/2005 | Mathis et al. | | | |
| 2005/0197692 | A1 | 9/2005 | Pai et al. | | | |
| 2005/0197693 | A1 | 9/2005 | Pai et al. | | | |
| 2005/0197694 | A1 | 9/2005 | Pai et al. | | | |
| 2005/0209690 | A1 | 9/2005 | Mathis et al. | | | |
| 2005/0216077 | A1 | 9/2005 | Mathis et al. | | | |
| 2005/0222678 | A1 | 10/2005 | Lashinski et al. | | | |
| 2005/0261704 | A1 | 11/2005 | Mathis | | | |
| 2005/0272969 | A1 | 12/2005 | Alferness et al. | | | |
| 2006/0020335 | A1 | 1/2006 | Kowalsky et al. | | | |
| 2006/0030882 | A1 | 2/2006 | Adams et al. | | | |
| 2006/0041305 | A1 | 2/2006 | Lauterjung | | | |
| 2006/0116758 | A1 | 6/2006 | Swinford et al. | | | |
| 2006/0142854 | A1 | 6/2006 | Alferness et al. | | | |
| 2006/0161169 | A1 | 7/2006 | Nieminen et al. | | | |
| 2006/0167544 | A1 | 7/2006 | Nieminen et al. | | | |
| 2006/0173536 | A1 | 8/2006 | Mathis et al. | | | |
| 2006/0191121 | A1 | 8/2006 | Gordon | | | |
| 2006/0271174 | A1* | 11/2006 | Nieminen et al. .......... 623/2.36 | | | |
| 2006/0276891 | A1* | 12/2006 | Nieminen et al. .......... 623/2.37 | | | |
| 2007/0027533 | A1* | 2/2007 | Douk ........................ 623/2.11 | | | |
| 2007/0055293 | A1 | 3/2007 | Alferness et al. | | | |
| 2007/0066879 | A1 | 3/2007 | Mathis et al. | | | |

FOREIGN PATENT DOCUMENTS

| | | |
|---|---|---|
| EP | 0903100 A1 | 3/1999 |
| EP | 0968688 A1 | 1/2000 |
| EP | 1050274 A1 | 11/2000 |
| EP | 1095634 A2 | 5/2001 |
| GB | 0741604 | 12/1955 |
| JP | 2754067 | 3/1998 |
| JP | 2000-308652 | 11/2000 |
| JP | 2001-503291 | 3/2001 |

OTHER PUBLICATIONS

Mathis et al., U.S. Appl. No. 11/782,508, entitled "Device and method for modifying the shape of a body organ," filed Jul. 24, 2007.
Mathis et al., U.S. Appl. No. 11/782,527 entitled "Device and method for modifying the shape of a body organ," filed Jul. 24, 2007.
Mathis et al; U.S. Appl. No. 11/963,417 entitled "Device and method for modifying the shape of a body organ," filed Dec. 21, 2007.
Mathis et al.; U.S. Appl. No. 12/016,054 entitled "Fixed anchor and pull mitral valve device and method," filed Jan. 17, 2008.
Gordon et al.; U.S. Appl. No. 11/971,174 entitled "Medical device delivery system," filed Jan. 8, 2008.
Nieminen et al; U.S. Appl. No. 12/060,781 entitled "Tissue shaping device," filed Apr. 1, 2008.
Pai, Suresh; U.S. Appl. No. 60/329,694 entitled "Percutaneous cardiac support structures and deployment means," filed Oct. 16, 2001.
Mathis, Mark; U.S. Appl. No. 11/655,710, entitled "Mitral Valve Device Using Conditioned Shape Memory Alloy," filed Jan. 18, 2007.
Gray, H. Anatomy of the Human Body. The Systemic Veins. Philadelphia: Lea & Febiger, 1918; Bartleby.com. 2000. Available at www.bartleby.com/107/. Accessed Jun. 7, 2006.
Heartsite.com. Echocardiogram, 1999; p. 1-4, A.S.M. Systems Inc. Available at: http://www.heartsite.com/html/echocardiogram.html. Accessed Jul. 1, 2005.
Papageorgiou, P., et al. Coronary Sinus Pacing Prevents Induction of Atrial Fibrillation. Circulation. 1997; 96(6): 1893-1898.
Webb, et al. Percutaneous transvenous mitral annuloplasty initial human experience with device implantation in the coronary sinus. Circulation. 2006; 851-855.
Hayner et al.; U.S. Appl. No. 12/189,527 entitled "Catheter cutting tool," filed Aug. 11, 2008.
El-Maasarany et al.; The coronary sinus conduit function: Anatomical study (relationship to adjacent structures); http://europace.oxfordjournals.org/cge/content/full/7/5/475. (accessed Sep. 9, 2008).

* cited by examiner

MITRAL VALVE ANNULOPLASTY DEVICE WITH VENA CAVA ANCHOR

BACKGROUND OF THE INVENTION

The mitral valve is located between the chambers of the left atrium and the left ventricle. When the left ventricle contracts to pump blood throughout the body, the mitral valve closes to prevent blood from being pumped back into the left atrium. In patients suffering from mitral valve regurgitation the mitral valve fails to properly close upon each contraction due to, for example, genetic malformation, disease, or injury, and blood is pumped back into the atrium. Mitral valve regurgitation is a serious, often rapidly deteriorating, condition that reduces circulatory efficiency.

Two of the more common techniques for restoring damaged mitral valve function are surgical replacement of the valve with a mechanical valve and implantation of a flexible ring around the native valve to support it. Each of these procedures is highly invasive as access to the heart is gained through an opening in the patient's chest. Patients with mitral valve regurgitation are often relatively frail which increases the risks associated with such an invasive operation.

A device to perform mitral valve annuloplasty is therefore needed that can be performed percutaneously without opening the chest wall. The anatomy of the heart and the coronary vasculature, including vessel length and diameter, can vary from patient to patient. Thus, a device to perform mitral valve annuplasty is also needed that can be performed on a variety of patients, regardless of the anatomy of their heart.

SUMMARY OF THE INVENTION

One aspect of the present invention is an intravascular device for performing percutaneous mitral valve annuloplasty. In preferred embodiments of the invention, the device includes a first anchor adapted to be anchored to the walls of a coronary sinus and a second anchor adapted to be anchored to the walls of a superior vena cava, with a support structure connecting the two anchors. The support structure may exert pressure on the coronary sinus wall, thus altering the shape of a mitral valve annulus.

In some embodiments the device includes an anchor lock adapted to lock the first anchor in an expanded configuration against the coronary sinus wall. In some embodiments the device includes an anchor lock adapted to lock the second anchor in an expanded configuration against the superior vena cava.

In some embodiments the device includes a coupler adapted to couple the device to a delivery tool which can be used to deliver the device to a desired location with the patient. In some embodiments the coupler has a tether and hitch wire for connecting a delivery tool to the device. In some embodiments the coupler is adapted to release the device from the delivery tool after it has been properly positioned inside the patient.

In some embodiments the device is adapted to be recaptured back into the catheter after the device is anchored within the patient.

Another aspect of the invention is to a method of performing mitral valve annuloplasty comprising anchoring a first anchor of a mitral valve annuloplasty device in a coronary sinus and anchoring a second anchor of the mitral valve annuloplasty device in a superior vena cava, wherein the mitral valve annuloplasty device further comprising a support structure disposed between and operatively connecting the first and the second anchors.

In some embodiments the method further comprises delivering the mitral valve annuloplasty device endovascularly. In some embodiments the delivering step comprises delivering the device to a patient's heart via a catheter.

In some embodiments the first anchoring step comprises expanding the first anchor from a delivery configuration to a deployed configuration in which the first anchor engages the coronary sinus. In some embodiments the method further comprises locking the first anchor in the deployed configuration. In some embodiments the second anchoring step comprises expanding the second anchor from a delivery configuration to a deployed configuration in which the second anchor engages the superior vena cava. In some embodiments the method comprises locking the second anchor in the deployed configuration.

In some embodiments the device may be recaptured after anchoring the device. In some embodiments the capturing step comprises advancing a catheter distally over the first anchor to place the first anchor inside the catheter in the delivery configuration. In some embodiments the recapturing comprises capturing the second anchor within the catheter after the second anchoring step.

In preferred embodiments a proximally directed force is applied on the mitral valve annuloplasty device after the first anchoring step.

In some embodiments the device is uncoupled from a delivery tool after the second anchoring step. In some embodiments the uncoupling comprises releasing a hitch wire from the device and then removing a tether from the device thereby uncoupling the device from the delivery tool.

INCORPORATION BY REFERENCE

All publications and patent applications mentioned in this specification are herein incorporated by reference in their entirety to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention relates to a medical device and uses thereof that supports or changes the shape of tissue near a vessel in which the device is placed. The present invention is particularly useful in reducing mitral valve regurgitation by changing the shape of or supporting a mitral valve annulus. In preferred embodiments, the device comprises a distal anchor adapted to be anchored in the coronary sinus and a proximal anchor adapted to be anchored in the superior vena cava, with a support structure disposed between the anchors. The length and diameter of a coronary sinus differ from patient to patient, and it is desirable for an intravascular device to function effectively in all patients, regardless of these differences. By anchoring the proximal anchor in the superior vena cava, the distal anchor may be positioned in the coronary sinus at a desired location to reduce mitral valve regurgitation without producing other adverse consequences to the patient. The superior vena cava anchor helps the intravascular device remain locked in place without limiting the coronary sinus anchor's available anchor locations. A patient-independent device is thus created. Although the embodiments of the invention described are designed to support a mitral valve annulus, those skilled in the art will appreciate that the invention is not limited to such a use.

Figure 1:
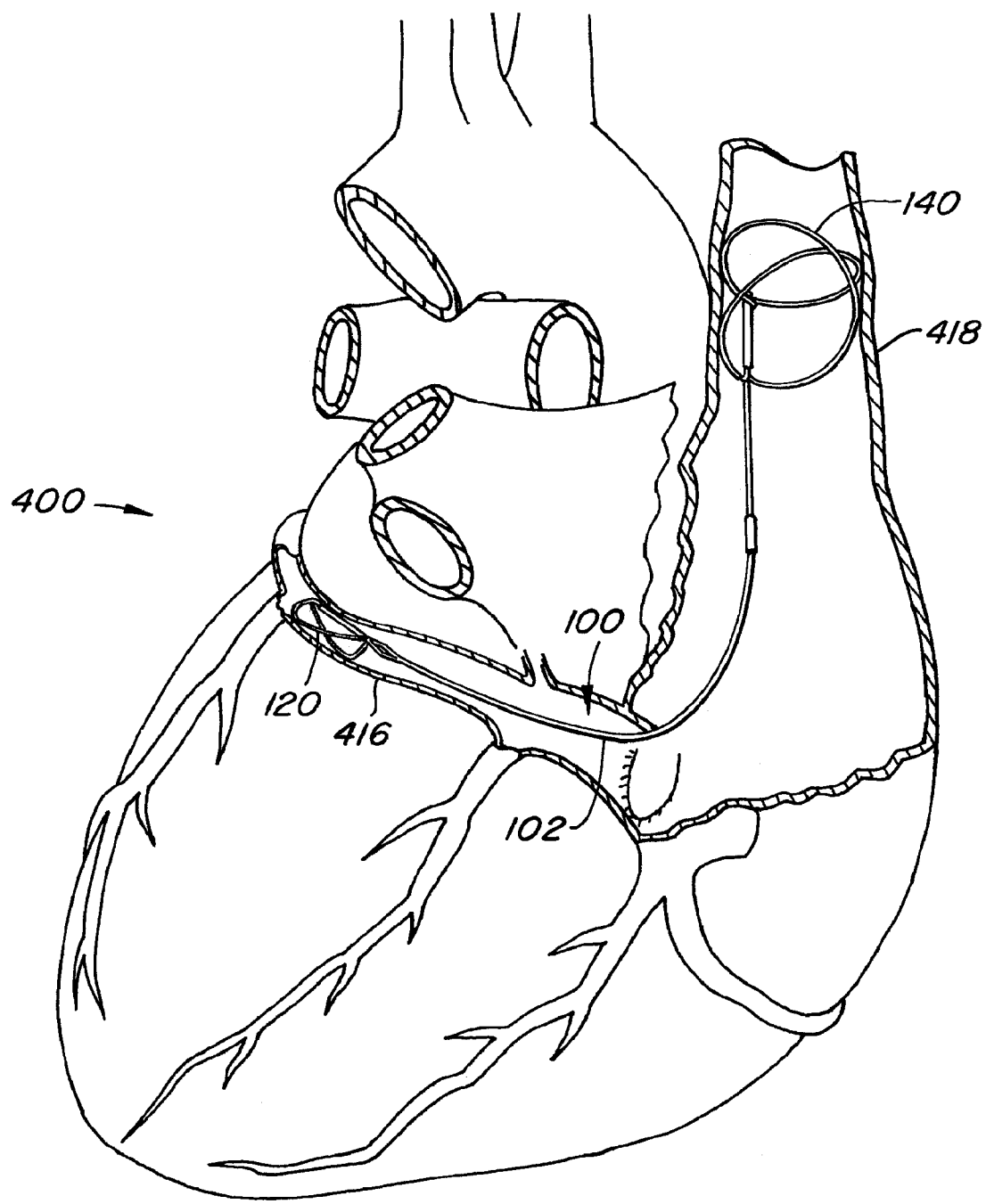
FIG. 1 is shows an embodiment of the invention anchored in the heart.

FIG. 1 is a posterior view of the heart 400 showing one embodiment of the invention with distal anchor 120 of intravascular device 100 anchored in coronary sinus 416, while proximal anchor 140 of intravascular device 100 is anchored in superior vena cava 418. Support structure 102 is disposed between the anchors.

Figure 2:
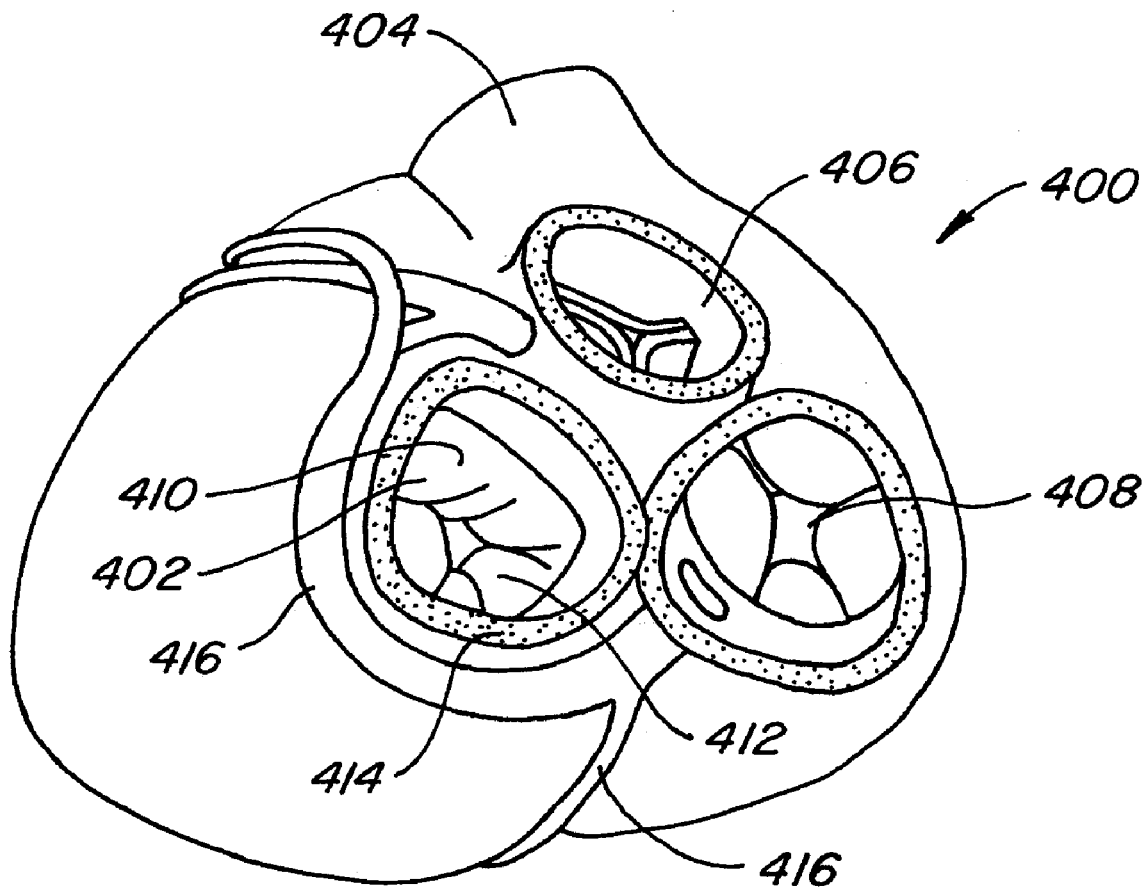
FIG. 2 is a superior view of the heart with the atria removed.

FIG. 2 is a superior view of the heart 400 with the atria removed. As pictured, the heart comprises several valves including mitral valve 402, pulmonary valve 404, aortic valve 406 and tricuspid valve 408. Mitral valve 402 includes anterior cusp 410, posterior cusp 412, and annulus 414. Annulus 414 encircles cusps 410 and 412 and functions to maintain their respective spacing to ensure complete mitral valve closure during left ventricular contractions of the heart 400. As illustrated, coronary sinus 416 partially encircles mitral valve 402 and is near mitral valve annulus 414. Coronary sinus 416 is part of the venous system of heart 400 and extends along the AV groove between the left atrium and the left ventricle. This places coronary sinus 416 essentially within the same plane as mitral valve annulus 414, making coronary sinus 416 available for placement of an intravascular device in order to affect mitral valve geometry and to restore proper valve function.

Figure 3:
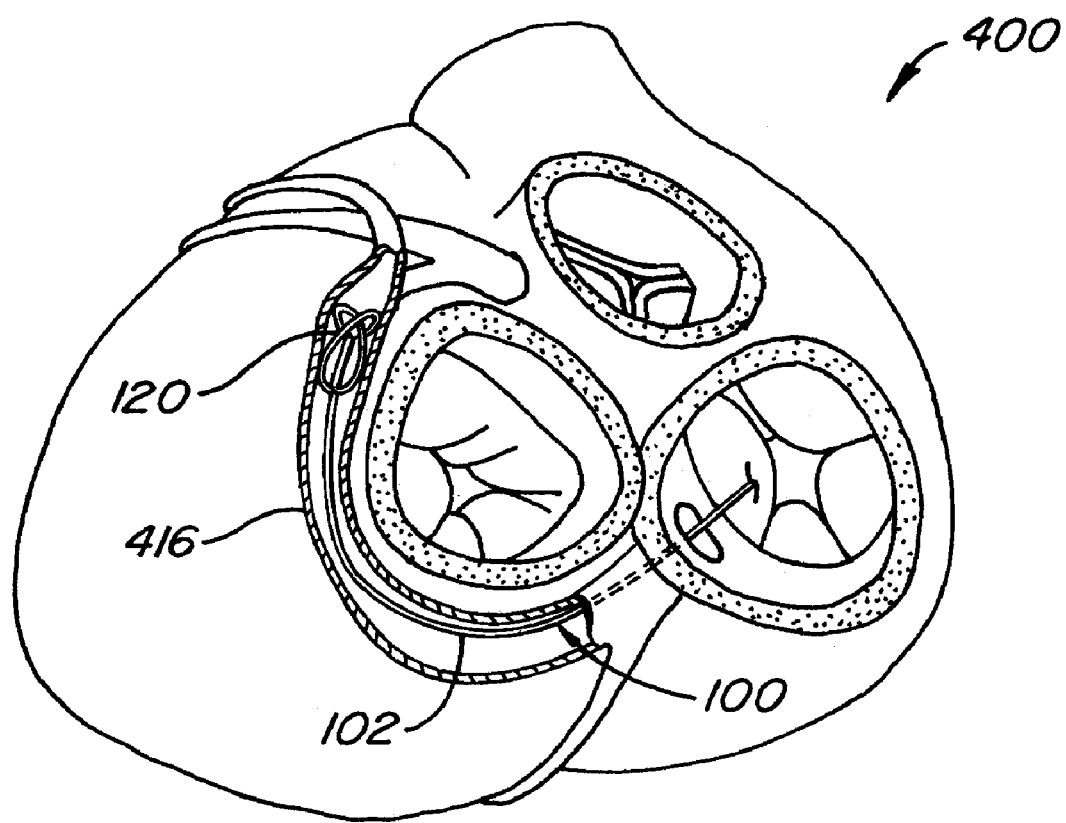
FIG. 3 illustrates a distal anchor of the present device anchored in the coronary sinus.

FIG. 3 illustrates one embodiment of distal anchor 120 of intravascular device 100 deployed and anchored within coronary sinus 416. Support structure 102 is disposed between distal anchor 120 and a proximal anchor (not shown) which is anchored in the superior vena cava (not shown).

Figure 4:
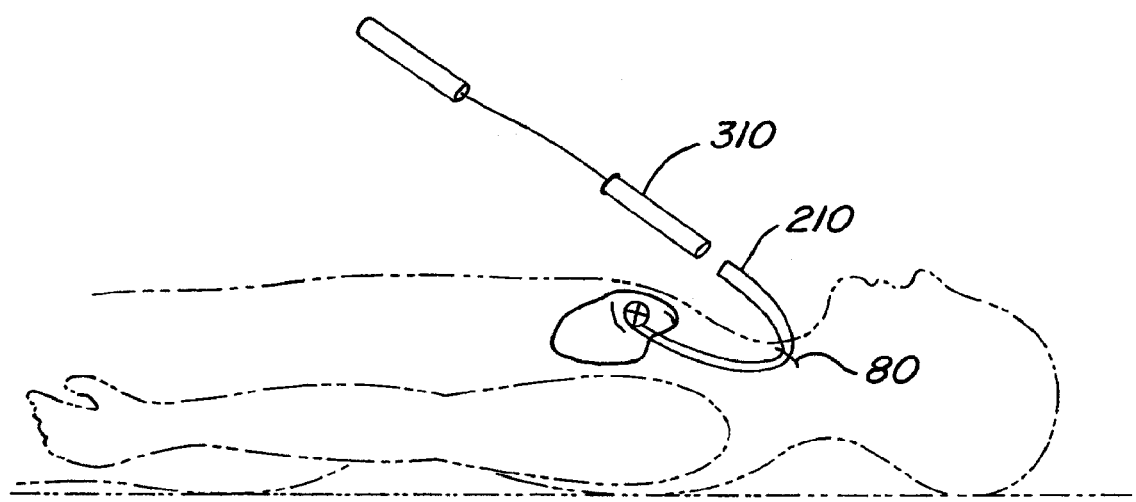
FIG. 4 illustrates one method of deploying an intravascular support.

FIG. 4 illustrates one embodiment of delivering the intravascular device of the present invention to a desired location within a patient's body. An incision 80 is made in the patient's skin to gain access to a blood vessel. The blood vessel may be, for example, the jugular vein. A guide catheter 210 is advanced through the patient's vasculature until its distal end is positioned near the desired location for the intravascular device. After positioning the guide catheter 210, a delivery catheter and advancing mechanism 310 are inserted through the guide catheter 210 to deploy the intravascular device at the desired location in the patient's body. In preferred embodiments, the delivery catheter is advanced until its distal end is inside the coronary sinus. Further detail regarding a suitable delivery system and advancing mechanism are described in commonly assigned U.S. patent application Ser. No. 10/946,332, filed Sep. 20, 2004.

In preferred embodiments, the distal end of the intravascular device is delivered to a location within the coronary sinus. The distal anchor is then deployed from the delivery catheter, then expanded to engage the coronary sinus wall and locked in place within the vessel. A proximal cinching force is then applied on the distal anchor from, for example, a tether connected to a delivery device as described herein below, until an appropriate amount of reshaping of the mitral valve or other tissue has occurred. While maintaining the cinching force, the proximal anchor is deployed from the delivery catheter, expanded and locked in an expanded configuration. A tether, for example, as described below, can then be released from the intravascular device.

In some embodiments the length of the intravascular device is between about 10 cm and about 20 cm. In preferred embodiments the length of the intravascular device is between about 12 cm and about 18 cm. In more preferred embodiments the length is about 15 cm.

Figure 5:
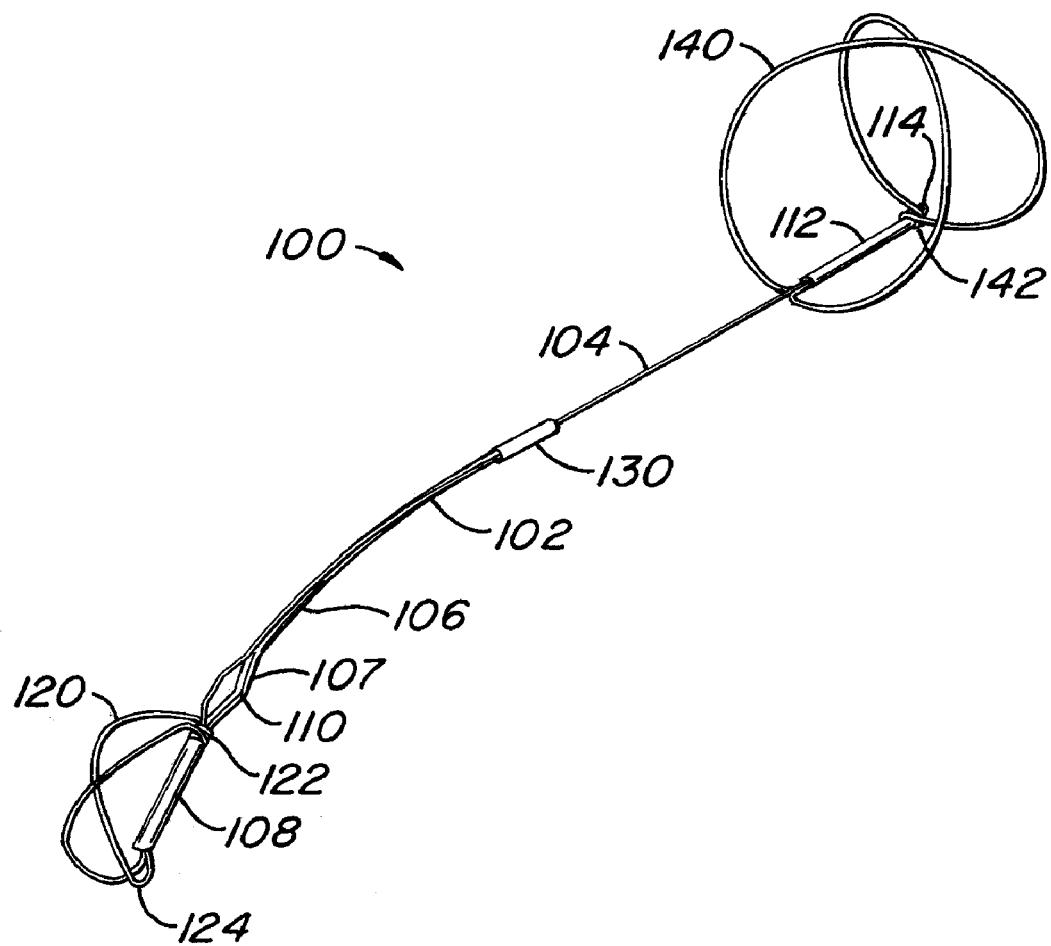
FIG. 5 illustrates one embodiment of the intravascular device.

FIG. 5 illustrates one embodiment of an intravascular device in accordance with the present invention. The intravascular device 100 includes a distal anchor 120, a proximal anchor 140 and a connector or support structure 102 extending between the anchors. In this embodiment, the support structure 102 has a first portion 104 formed from nitinol wire or other biocompatible material extending between a distal crimp 108 and a proximal crimp 112. A second portion of the support structure is a substantially flat ribbon section 106 extending between distal crimp 108 and a central crimp 130. A bent portion 107 of ribbon section 106 interacts with wire portion 104 to form a distal anchor lock 110. Distal lock 110 interacts with a distal lock loop 122 to secure the distal anchor in an expanded configuration. Proximally located to proximal crimp 112 is an arrowhead-shaped proximal lock 114 that interacts with proximal lock loop 142 to lock the proximal anchor 140 in place in a manner described herein. Expanded proximal and distal anchors 140 and 120 are configured in a FIG. 8 pattern as is shown in FIGS. 5 and 6.

Figure 6:
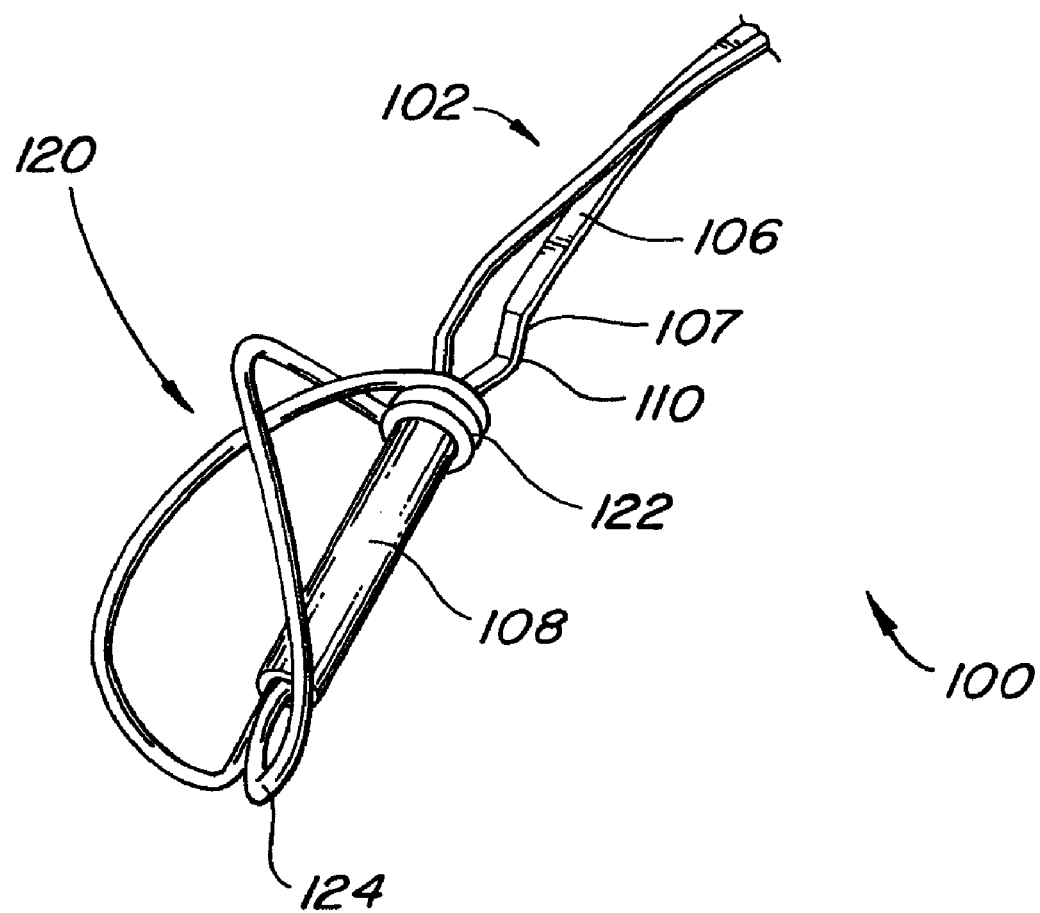
FIG. 6 details a distal end of an intravascular device.

As is shown in FIGS. 5 and 6, the wire forming the distal anchor 120 has one end positioned within the distal crimp 108. After exiting the distal end of the distal crimp 108, the wire forms a figure eight configuration by bending radially outward from the longitudinal axis of the distal crimp 108 and distally from the distal crimp 108. The wire then bends back proximally and radially inward and crosses the longitudinal axis of the distal crimp 108 to form one leg of the figure eight. The wire is then bent around the longitudinal axis of the support structure 102 to form a distal lock loop 122 before extending radially outwards and distally back over the longitudinal axis of the distal crimp 108 to form the other leg of the figure eight. Finally, the wire is bent proximally into the distal end of the distal crimp 108, forming the distal anchor 120. The distal ends 124 of the distal anchor wire may extend down from crimp 108 to provide for strain relief while the anchor is compressed for storage or delivery. Details of this feature may be found in U.S. application Ser. No. 11/275,630, filed Jan. 19, 2006.

The distal anchor is expanded by sliding the distal lock loop 122 from a position proximal to the distal lock 110 to a position that is distal to the distal lock 110 as can be seen in FIGS. 5 and 6. The distal lock 110 provides camming surfaces for a locking action. Distal sliding of distal lock loop 122 over distal lock 110 pushes these camming surfaces inward to permit loop 122 to pass distally over lock 110, then return to their original spacing to retain loop 122 in a locked position.

The dimensions of the distal and proximal anchors are selected to effectively engage the walls of the lumens in which they are deployed. In some embodiments, the deployed height of the distal anchor is between about 7 mm and about 18 mm. When treating mitral valve regurgitation by placing the distal anchor of the intravascular device in the coronary sinus, the diameter of the vessel may expand over time post-deployment. Creating an oversized anchor combined with the inherent deformability and recoverability properties of the anchor material (particularly nitinol or some other shape memory material as described herein) enables the anchor to continue to expand from its initial deployment size as the lumen distends and expands over time. The wire used to form the distal anchor 120 is preferably formed of a biocompatible, elastic wire such as stainless steel or a shape memory material such as nitinol having a diameter of between 0.0110 inches and 0.020 inches and most preferably about 0.0160 inches.

At the proximal end of the intravascular support 100 is a proximal anchor 140 that is preferably formed of a biocompatible, elastic wire such as stainless steel or a shape memory material such as nitinol. As shown in FIG. 5, the proximal anchor 140 in one embodiment is made of a single length of wire having a first end positioned within a proximal crimp 112. The wire extends distally from the proximal crimp 112 and bends radially outward from the longitudinal axis of the proximal crimp 112 before being bent proximally and crossing the longitudinal axis of the proximal crimp 112 in order to form a first leg of a figure eight configuration. The wire is then bent to form a proximal double loop eyelet 142 around the longitudinal axis of the support structure 102 wherein the proximal lock loop 142 has a diameter that allows it to be forced over the proximal lock 114. After forming the proximal lock loop 142, the wire extends radially outward from the longitudinal axis of the proximal crimp 112 before being bent distally over and across the longitudinal axis of the proximal crimp 112 to form the second leg of a figure eight. Finally, the wire is bent proximally and extends into the distal end of the proximal crimp 112. The proximal side of proximal anchor 140 may be provided with variable slope recapture features, as described in U.S. patent application Ser. No. 10/429,172, filed May 2, 2003.

Similar to the distal anchor, the proximal anchor is expanded and locked by sliding the proximal double loop eyelet of the proximal anchor from a position proximal to the proximal lock 114 to a position that is distal to the proximal lock 114. The proximal lock 114 has an "arrowhead" shape whereby it is easier to advance the proximal lock loop 142 over the lock in the distal direction than to retrieve the proximal lock loop 142 over the proximal lock 114 in the proximal direction. Distal movement of proximal lock loop 142 cams the proximal surfaces radially inward to permit loop 142 to pass distally of the proximal lock 114, then return to their original spacing to keep proximal lock loop 142 in a locked position.

In a preferred embodiment, the proximal anchor has a larger radius of curvature than the distal anchor because it is designed to fit within a larger diameter vessel, for example, the superior vena cava. The proximal anchor is configured so as to engage the walls of the superior vena cava. In some embodiments, the deployed height of the proximal anchor is between about 18 mm and about 40 mm. Similar to the distal anchor, combining an oversized proximal anchor with the inherent deformability and recoverability properties of the anchor material (particularly nitinol or some other shape memory material as described herein) enables the proximal anchor to continue to expand from its initial deployment size as the vessel wall may distend and expand over time.

Upon expansion, the proximal anchor circumferentially engages the superior vena cava wall with a radially outwardly directed force that is distributed unequally around the circumference of the anchor by distending the vessel wall in variable amounts along the axial length of the proximal anchor. Similar to the distal anchor, the unequal distribution of force being applied helps the proximal anchor contact the lumen wall securely by creating bumps and ridges that are not parallel to the central axis of the vessel. Further details regarding expandable anchors for intravascular devices may be found in U.S. patent application Ser. No. 10/429,172, filed May 2, 2003, and Ser. No. 11/275,630, filed Jan. 19, 2006.

The support structure has a length that is selected based on its intended destination within a patient's vessel. For use in supporting a mitral valve, the support structure is preferably between about one and about six inches long and has a curved bend between its proximal end and distal end with a radius of curvature between about one and about six inches, or more preferably between about two and about five inches and with a radius of curvature of between about one inch and about three inches, or more preferably between about three and about four inches with a radius of curvature of between about 1.3 inches and about 1.5 inches. In some embodiments, the radius of curvature is greater than two, three, or four inches, and in other embodiments it is less than two, one, or 0.5 inches. In addition, the wire used to form the support structure is flexible enough to bend within the vasculature upon each heartbeat (thereby changing the force applied to the mitral valve annulus during the heartbeat) and at the same time strong enough to support the mitral valve. In one embodiment, the wire used to form the support structure is made of nitinol having a modulus of elasticity of about 5 to about $20 \times 10^6$ psi and a cross-sectional area between about $9.5 \times 10^{-5}$ $in^2$ to about $5.9 \times 10^{-4}$ $in^2$ and most preferably about $5.9 \times 10^{-4}$ $in^2$. Other shape memory materials may be used for support structure as well.

In one embodiment of the invention, the distal and proximal crimps are oriented such that the axes of the crimps are offset with respect to each other by an angle of at least about 10, about 15, about 20, about 25, or about 30 degrees. The offset helps the support structure seat itself in the coronary sinus surrounding the mitral valve. However, proximal and distal crimps may be offset by more or less depending upon the anatomy of the intended destination of the anchors.

In some embodiments, the wires comprising the anchors and the support structure are not the same. The anchors may be attached to the support structure by an attaching wire, such as nitinol wire or other shape memory material. The attaching wire may be spiral wrapped around the base of each anchor and further wrapped around the support structure to attach the anchors to the support structure. In another embodiment, each anchor may be attached to the support structure by wrapping an end of the anchor wire around the support structure. In yet another embodiment, the two anchors and the support structure may be made from a single wire, such as nitinol wire or other shape memory material. In any of the embodiments herein, the support wire may be coated with a biodegradable material that allows for additional contraction or other shape adjustment after it bends.

Figure 7:
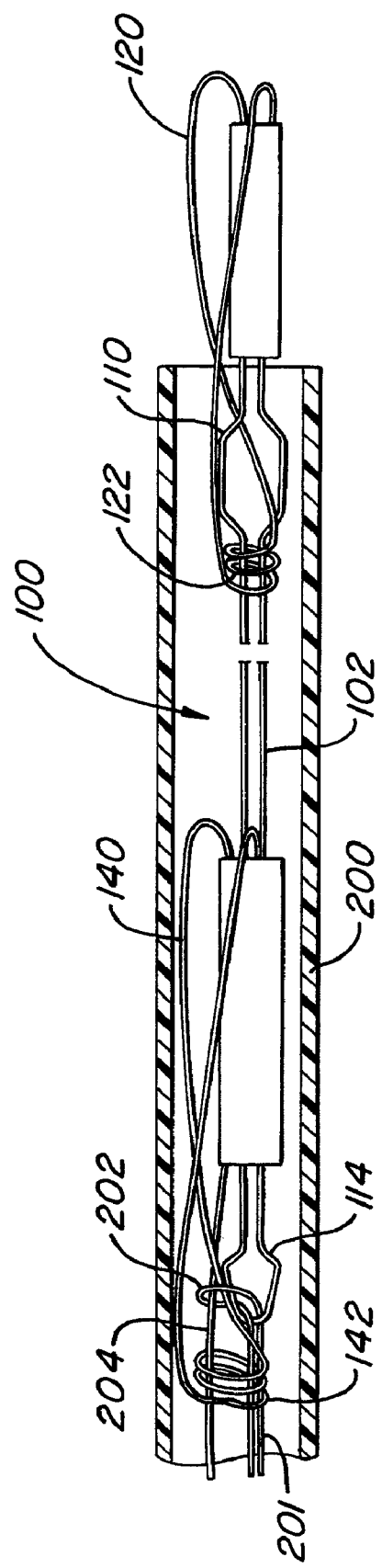
FIG. 7 illustrates a coupler coupled to an intravascular device.

In some embodiments the intravascular device comprises a coupler adapted to couple the intravascular device to a delivery tool. FIG. 7 illustrates an exemplary coupler in accordance with the present invention. A coupler comprises a loop 202 at the end of tether 201 and a hitch wire 204. Loop 202 extends through proximal lock 114, and the hitch wire 204 passes through loop 202 and into the proximal crimp 104, thereby preventing loop 202 from being withdrawn from proximal lock 114.

Figure 8:
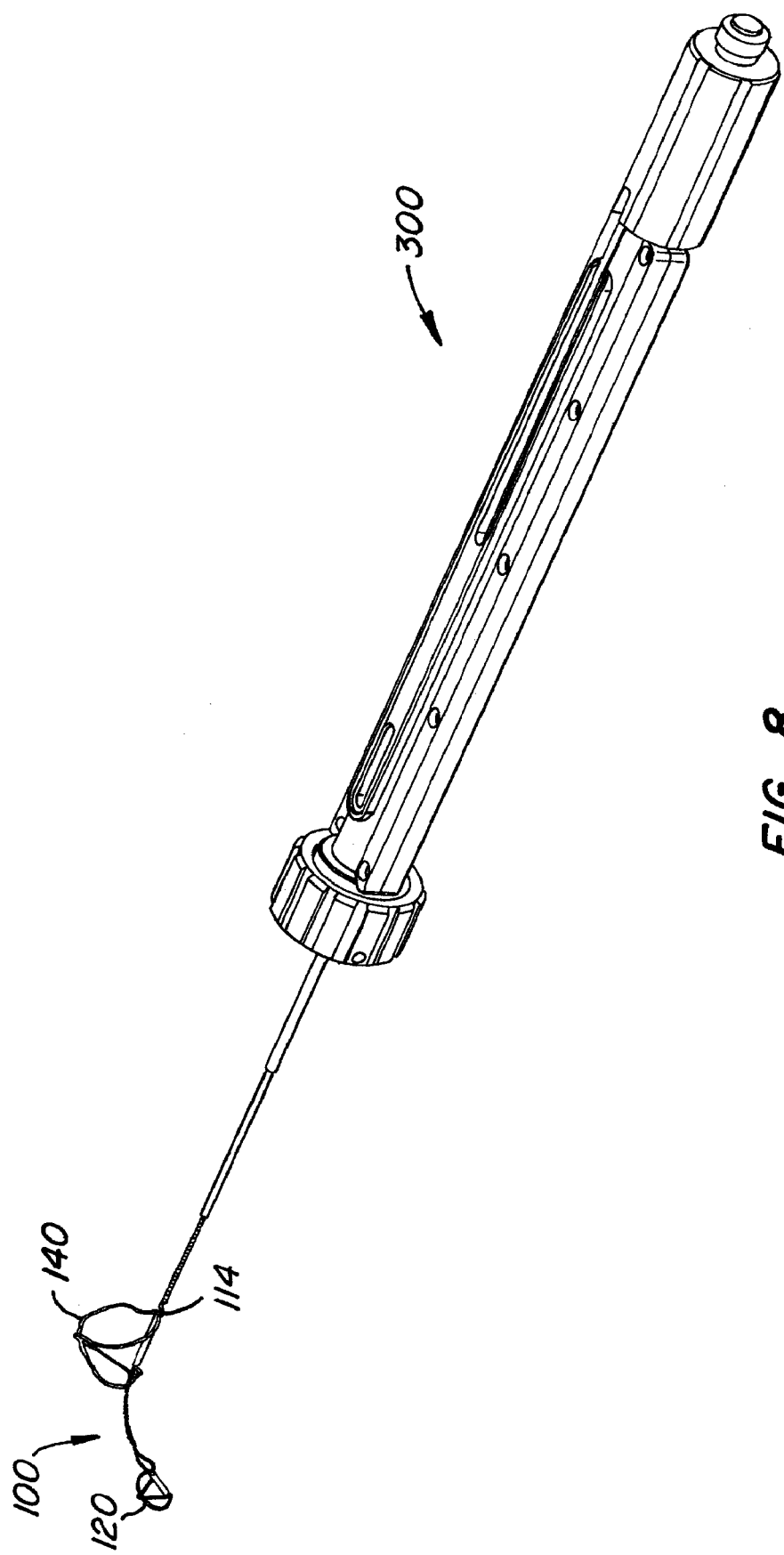
FIG. 8 illustrates a delivery tool for delivering the intravascular device.

FIG. 8 shows an exemplary delivery tool 300 that may be used to deliver and deploy an intravascular device 100 via a catheter (not shown). Details of the operation of delivery tool 300 may be found in U.S. patent application Ser. No. 10/946,332, filed Sep. 20, 2004.

Again referring to FIG. 7, an exemplary method of performing mitral valve annuloplasty on a patient's heart is described. As indicated above, the intravascular device 100 is preferably loaded into and delivered to a desired location within a catheter 200 with the proximal and distal anchors 140 and 120 in a delivery or collapsed condition. That is, the distal lock loop 122 of the distal anchor 120 is positioned proximally to the distal lock 110 and the proximal lock loop 142 of the proximal anchor 140 is positioned proximally to the proximal lock 114. Medical personnel may deploy the distal end of the intravascular device 100 from the catheter 200 into the lumen of a coronary sinus by advancing the intravascular device 100 or by retracting the catheter 200, or a combination thereof. A delivery tool (such as that of FIG. 8) may provide for distal movement of the intravascular device 100 with respect to catheter 200, and a tether 201 may provide proximal movement of the device 100 or for maintaining the position of the intravascular device 100 relative to distal motion of a catheter 200. Because of the inherent recoverability of the material from which it is formed, the distal anchor 120 begins to expand as soon as it is deployed from the catheter 200. Using the delivery tool, the distal lock loop 122 of the distal anchor is moved distally over the distal lock 110 so that the distal anchor 120 further expands and locks in place to securely engage the coronary sinus wall and remains in the locked expanded configuration. Next, the intravascular device 100 is tensioned by pulling on the tether to apply a proximally-directed cinching force on the distal anchor 120, thereby modifying the shape of the coronary sinus and adjacent nearby valve annulus tissue. Fluoroscopy, ultrasound or other imaging technology may be used to detect when the device modifies the shape of the mitral valve annulus sufficiently to reduce mitral valve regurgitation without otherwise adversely affecting the patient. A preferred method of assessing efficacy and safety during a mitral valve procedure is disclosed in co-pending U.S. patent application Ser. No. 10/366,585, filed Feb. 12, 2003. Once the device has been sufficiently cinched, the proximal anchor 140 is deployed from the catheter to begin expansion. In preferred embodiments, the proximal anchor is deployed in the superior vena cava to at least increase the possible locations in which the distal anchor may be positioned. The proximal lock loop 142 of the proximal anchor 140 is advanced distally over the proximal lock 114 by the delivery tool to further expand and lock the proximal anchor 140, thus engaging the superior vena cava wall and maintaining a cinching force of the device on the mitral valve annulus. Finally, the coupler that couples the intravascular device to a delivery tool can be released. A hitch wire 204 is first withdrawn (by, for example, a hitch wire actuator of the delivery tool of FIG. 8), thereby releasing the loop 202 so it can be pulled through the proximal lock 114, and thereby uncoupling the intravascular device from the delivery tool.

In some embodiments it may be necessary to move or remove the intravascular device after deployment by recapturing the device into a catheter. After the distal anchor is deployed and prior to initial deployment of the proximal anchor, the distal anchor may be recaptured into the delivery catheter by holding the intravascular device in place with a the tether while advancing the catheter distally over the distal anchor so that the entire intravascular device is once again inside the catheter. The distally directed force of the catheter collapses the distal anchor into its delivery configuration to ease recapture into the catheter. In some embodiments the tether may be used to pull the intravascular device proximally while holding the catheter stationary. Either motion, or a combination of motions, may be used to recapture the distal anchor. Similarly, after deploying the second anchor but prior to releasing the coupler as described above herein, the intravascular device may be captured into the delivery catheter by holding the device in place with the tether while advancing a catheter distally first over a proximal anchor, over the support structure, and finally over a distal anchor. The distally directed force of the catheter collapses the anchors such that they can again fit within the catheter in their delivery configuration. The tether may also be used to pull the device proximally, while holding the catheter stationary. If the coupler has been detached from the device prior to capture, the device may be recaptured into the delivery catheter or another catheter by grasping the proximal end of the device with a tether or grasper and by advancing the catheter distally over the device. Any of these methods allow for repositioning one or both anchors as well as repositioning the entire intravascular device as may be required.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for performing percutaneous mitral valve annuloplasty comprising:
   a first anchor adapted to be deployed by a catheter to engage a wall of a coronary sinus;
   a second anchor adapted to be deployed by the catheter to engage a wall of a superior vena cava; and
   a support structure disposed between and operatively connecting the first anchor and the second anchor.

2. The device of claim 1 further comprising an anchor lock adapted to lock the first anchor in an expanded configuration.

3. The device of claim 1 further comprising an anchor lock adapted to lock the second anchor in an expanded configuration.

4. The device of claim 1 further comprising a coupler adapted to couple the device to a delivery tool.

5. The device of claim 4 wherein the coupler comprises a tether and a hitch wire.

6. The device of claim 4 wherein the coupler is further adapted to release the device from the delivery tool.

7. The device of claim 1 wherein the second anchor is expandable and has a collapsed delivery configuration and an expanded deployed configuration, and wherein the second anchor is adapted to engage the wall of the superior vena cava in the expanded deployed configuration.

8. A device for performing percutaneous mitral valve annuloplasty comprising:
   a first anchor adapted to be deployed by a catheter to engage a wall of a coronary sinus;
   a second anchor adapted to be deployed by the catheter to engage a wall of a superior vena cava; and
   a support structure disposed between and operatively connecting the first anchor and the second anchor, wherein the device is adapted to be recaptured by the catheter.

9. A method of performing mitral valve annuloplasty on a patient's heart comprising:
   anchoring a first anchor of a mitral valve annuloplasty device in a coronary sinus;

anchoring a second anchor of the mitral valve annuloplasty device in a superior vena cava, the mitral valve annuloplasty device further comprising a support structure disposed between and operatively connecting the first and the second anchors, and applying a proximally directed force on the mitral valve annuloplasty device after the first anchoring step.

10. The method of claim 9 further comprising delivering the mitral valve annuloplasty device endovascularly.

11. The method of claim 10 wherein the delivering step comprises delivering the device to a patient's heart via a catheter.

12. The method of claim 11 further comprising capturing the first anchor within the catheter after the first anchoring step.

13. The method of claim 12 wherein the capturing step comprises advancing a catheter distally over the first anchor to place the first anchor inside the catheter in the delivery configuration.

14. The method of claim 11 further comprising capturing the second anchor within the catheter after the second anchoring step.

15. The method of claim 14 wherein the capturing step comprises advancing a catheter distally over the second anchor to place the second anchor inside the catheter in the delivery configuration.

16. The method of claim 9 wherein the first anchoring step comprises expanding the first anchor from a delivery configuration to a deployed configuration in which the first anchor engages the coronary sinus.

17. The method of claim 16 further comprising locking the first anchor in the deployed configuration.

18. The method of claim 9 wherein the second anchoring step comprises expanding the second anchor from a delivery configuration to a deployed configuration in which the second anchor engages the superior vena cava.

19. The method of claim 18 further comprising locking the second anchor in the deployed configuration.

20. The method of claim 9 further comprising uncoupling the device from a delivery tool after the second anchoring step.

21. The method of claim 20 where the uncoupling comprises releasing a hitch wire from the device and removing a tether from the device thereby uncoupling the device from the delivery tool.

* * * * *